United States Patent [19]
Gautier et al.

[11] Patent Number: 4,855,025
[45] Date of Patent: Aug. 8, 1989

[54] POLYFLUORO COMPOUNDS AND METHOD FOR PREPARING THEM

[75] Inventors: Martine Gautier, Toulouse; Isabelle Rico; Armand Lattes, both of Ramonville; René Bertocchio, Vourles, all of France

[73] Assignee: Societe Atochem, Puteaux, France

[21] Appl. No.: 111,188

[22] Filed: Oct. 22, 1987

[30] Foreign Application Priority Data

Oct. 24, 1986 [FR] France .............................. 86 14811
Feb. 17, 1987 [FR] France .............................. 87 02009

[51] Int. Cl.$^4$ .............................................. C07G 13/00
[52] U.S. Cl. ........................... 204/157.86; 204/157.87; 204/157.89; 204/158.12; 564/209; 562/605
[58] Field of Search ..................... 564/209; 562/605; 204/157.86, 157.87, 157.89, 158.12

[56] References Cited

U.S. PATENT DOCUMENTS

| | | | |
|---|---|---|---|
| 2,701,814 | 2/1955 | Smith | 526/248 X |
| 2,951,051 | 8/1960 | Tiers | 526/245 X |
| 3,133,965 | 5/1964 | Amann et al. | 564/209 |
| 3,153,670 | 10/1964 | Speziale et al. | 564/209 X |
| 3,423,465 | 1/1969 | Andreades et al. | 562/605 X |
| 3,535,369 | 10/1970 | Sianesi | 564/209 X |
| 4,073,817 | 2/1978 | Horst | 568/822 X |
| 4,124,469 | 11/1978 | Bathelt | 204/157.89 |
| 4,429,154 | 1/1984 | Baasner et al. | 564/209 X |

FOREIGN PATENT DOCUMENTS

| | | | |
|---|---|---|---|
| 3219075 | 12/1982 | Fed. Rep. of Germany . | |
| 55/35020 | 3/1980 | Japan | 564/209 |
| 60/158134 | 8/1985 | Japan | 564/209 |
| 1381570 | 1/1975 | United Kingdom . | |

*Primary Examiner*—Stephen J. Kalafut
*Attorney, Agent, or Firm*—Stevens, Davis, Miller & Mosher

[57] ABSTRACT

This invention relates to compounds which simultaneously contain a perfluorinated chain and a hydrogenated chain and which correspond to the general formula:

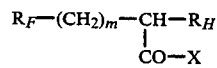

in which $R_F$ is a perfluoroalkyl radical, m an integer from 0 to 2, $R_H$ an alkyl radical, X an OH or $NR_1R_2$ group, and $R_1$ and $R_2$ are hydrogen atoms or methyl radicals. The amides ($X=NR_1R_2$) are prepared by photoamidation of the polyfluoroolefins $R_F-(CH_2)_p-CH=CH-C_nH_{2n+1}$ where p is equal to 0 or 1 and n is an integer from 1 to 17, and the acids ($X=OH$) are prepared by hydrolysis of the amides thus obtained.

The acids and their salts may be employed as surface-active agents or, as also the amides, as intermediates for the synthesis of such agents.

19 Claims, No Drawings

POLYFLUORO COMPOUNDS AND METHOD FOR PREPARING THEM

The invention relates to new compounds containing, at the same time, a perfluorinated chain ($R_F$) and a hydrogenated chain ($R_H$), which may be employed in particular as surface-active agents or as intermediates for the synthesis of such agents.

By virtue of their property of appreciably reducing the surface tension of aqueous solutions, fluorinated surfactants have found an especially important application in the development of extinguishing mixtures intended for combating fires and particularly those involving hydrocarbons. In the extinguishing compositions, the fluorinated surfactants are generally associated with nonfluorinated surfactants so as to form rapidly a resistant and durable film on the surfaces of the water-immiscible hydrocarbon. Although advantageous results can be obtained with mixtures of fluorinated and nonfluorinated surfactants, there is a continuing need to simplify the formulation of extinguishing compositions, for example by providing a single surfactant which simultaneously contains a perfluorinated chain and a hydrogenated chain.

With this in mind, the subject of the present invention is now mixed compounds containing a perfluorinated chain and a hydrogenated chain.

The compounds according to the invention may be denoted by the general formula:

in which $R_F$ denotes a linear or branched perfluoroalkyl radical containing from 1 to 20 carbon atoms, $R_H$ denotes a linear or branched alkyl radical containing from 1 to 18 carbon atoms, m is an integer from 0 to 2, and X denotes an OH or $NR_1R_2$ group in which $R_1$ and $R_2$ may be identical of different and each denotes a hydrogen atom or a methyl radical.

Particular preference is given to the compounds in which the radicals $R_F$ and $R_H$ contain from 4 to 12 carbon atoms and in which the nitrogen is unsubstituted ($R_1=R_2=H$).

The invention also includes the mixtures of two compounds of this type, one corresponding to the formula:

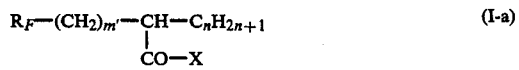

and the other to the formula:

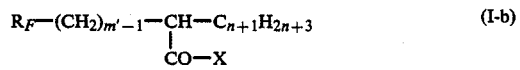

where m' is equal to 1 or 2 and n is an integer from 1 to 17, it being possible for the molar ratio I-a/I-b to range from 0.1 to 10.

The compounds according to the invention in which X is an $NR_1R_2$ group may be prepared by photoamidation of a polyfluoroolefin of general formula:

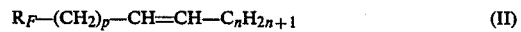

in which p is equal to 0 or 1 and n is an integer from 1 to 17, in the presence of an excess of formamide or of a methylated derivative thereof.

This reaction is preferably carried out by irradiating with ultraviolet light a mixture containing the polyfluoroolefin (II) and formamide or its methyl derivative in the presence of acetone as initiator. The operation may be performed in a homogeneous medium consisting of a solution of the reactants (olefin, formamide and acetone) in an inert organic solvent such as 2-methyl-1-propanol, 1,4-dioxane and, preferably, tert-butanol.

Except in the case of dimethylformamide, it is also possible to subject to UV rays a microemulsion of the reactants which is produced with the aid of a nonionic surface-active agent and a cosurfactant agent of the alcohol type, one of these two agents having to be fluorinated and the other unfluorinated. As nonionic surface-active agents which may be employed, more particular mention may be made of ethoxylated alkylphenols, ethylene and propylene oxide polycondensates (Pluronics) and ethoxylated polyfluoroalcohols. As examples of cosurfactants, there may be mentioned aliphatic alcohols such as hexanol, heptanol and octanol, and fluoroaliphatic alcohols of the $R_FC_2H_4OH$ type, such as 2-perfluorobutylethanol and its perfluorohexyl and perfluorooctyl homologues. To obtain a suitable microemulsion it is essential to employ the nonionic surfactant and the cosurfactant in such quantities that their mass ratio is between 0.5 and 1.5 and preferably substantially equal to 1. In this respect, the combination of a condensate of nonylphenol with 5 to 14 moles of ethylene oxide and of 2-perfluorobutylethanol, as well as the combination of a condensate of 2-perfluorohexylethanol with 10 to 15 mols of ethylene oxide and of 1-hexanol, 1-heptanol or 1-octanol, are particularly well suited.

The duration of the irradiation, which is preferably performed at a temperature ranging from 25° to 50° C., may vary within wide limits, depending on the intensity of irradiation, and is generally between 12 and 60 hours. The best yields are obtained with irradiation times ranging from 30 to 50 hours.

As indicated earlier, the operation is performed in the presence of an excess of formamide or of its methylated derivative. The molar ratio formamide (or methylated derivative)/olefin (II) may very within wide limits but, in order to promote the photoamidation reaction and to improve the yield, it is generally between 10 and 120, preferably between 40 and 90.

The quantity of acetone to be used as initiator may itself also vary within wide limits. Preferably, this quantity will be chosen so that the molar ratio acetone/formamide is between 0.03 and 0.2 and advantageously between 0.05 and 0.09.

Whatever the method chosen (homogeneous medium or microemulsion), the photoamidation of an olefin of formula II produces a mixture of the two amides of formulae:

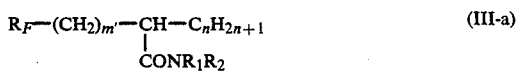

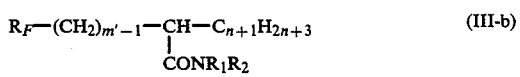

the symbols m', n, $R_F$, $R_1$ and $R_2$ having the same meanings as previously.

However, when the operation is performed in a homogeneous medium, the major product is always the amide III-a corresponding to the attachment of the carbamoyl group to the olefinic carbon furthest away from the perfluorinated chain. In microemulsion, the predominant product is in most cases the amide III-b corresponding to the amidation of the olefinic carbon closest to the perfluorinated chain. If desired, the amides III-a and III-b may be separated by means of usual methods such as extraction with fluorinated solvents (for example trichlorotrifluoroethane) or by preparative chromatography.

The starting polyfluoroolefins (II) are known substances. Those in which p is equal to zero, that is to say the olefins $R_F$—CH=CH—$C_nH_{2n+1}$, can generally be obtained by addition of a perfluoroalkyl iodide $R_FI$ to an olefin $C_nH_{2n+1}CH=CH_2$ (see G. V. D. Tiers, J. Org. Chem. 27, 2261, 1962 and N. O. Brace, J. Org. Chem. 37, 2429, 1972), followed by dehydroiodination of the iodohydrin formed $R_FCH_2CHI$—$C_nH_{2n+1}$ using alcoholic potassium hydroxide. Those in which p is equal to 1, that is to say the olefins $R_F$—$CH_2$—CH=CH—$C_nH_{2n+1}$, can be prepared by reaction of an aliphatic aldehyde with a 2-perfluoroalkylethyltriphenylphosphonium iodide, itself obtained by reacting triphenylphosphine with a 2-perfluoroalkylethyl iodide (see B. Escoula et al, Synth. Comm. 15(1), 35, 1985 and C. Cecutti et al, J. Dispersion Science and Technology, 7(3), 307, 1986).

The compounds according to the invention in which X is an OH group may be prepared by hydrolysis of the amides. This hydrolysis may be carried out in an aqueous medium using a base which is preferably sodium hydroxide but which may also be potassium hydroxide. The operation is carried out in a strong basic medium, 12 to 36N, preferably 20 to 30N at a temperature which may range from 100° to 160° C., but which is preferably between 120° and 140° C. The hydrolysis is considered to be complete after 24 hours. After the reaction mixture has been acidified, the acid formed may be isolated by conventional methods, in particular by extraction with a solvent chosen from chlorofluorohydrocarbons such as, for example, trichlorotrifluoroethane.

The acids according to the invention are oily or solid in form. They can be easily converted into water-soluble salts by means of conventional methods, for example by the action of an ethanolic solution of potassium hydroxide in the case of the potassium salts.

The polyfluorinated acids according to the invention and their salts may be employed as surface-active agents or, as also the amides, as intermediates for the synthesis of such agents.

The examples which follow illustrate the invention without limiting it. The reference employed for the $^{19}F$ NMR spectra is trifluoroacetic acid.

EXAMPLE 1

Preparation of 1,1,1,2,2,3,3,4,4-nonafluoropentadecane 6- and 7-carboxamides 0.744 g of the fluoroolefin $C_4F_9$—$CH_2$—CH=CH—$C_8H_{17}$, 5.88 ml of formamide, 15.84 ml of tert-butanol and 0.83 ml of acetone are introduced into a pyrex tube. The mixture is then degassed with a stream of argon for 5 minutes to remove atmospheric oxygen and then the tube is placed on a roundabout rotating in a circular enclosure covered with 16 UV lamps ($\lambda = 300$ nm; P = 16 W) which maintain a temperature of approximately 30°–35° C. The tube is left under ultraviolet irradiation for two days.

The precipitate of oxamide formed during the synthesis is then removed by filtration and then the filtrate is evaporated under vacuum (2,000 Pa) and the residue is taken up with 5 ml of water. A precipitate is formed and is purified by recrystallization from a mixture of equal volumes of acetone and petroleum ether, and is then dried over $P_2O_5$ is a desiccator (666 Pa).

This produces 0.57 g of a solid which melts at 80° C. and whose analyses ($^1H$ NMR, $^{19}F$ NMR and VPC) show that it corresponds to the isomers of formulae:

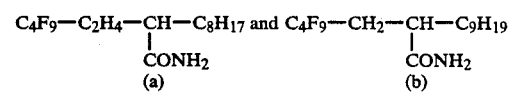

in the ratio a/b equal to 2.89.

EXAMPLE 2

Preparation of 1,1,1,2,2,3,3,4,4,5,5,6,6-tridecafluorotridecane 8- and 9-carboxamides The procedure is as in Example 1, but with 0.832 g of the fluoroolefin $C_6F_{13}$—$CH_2$—CH=CH—$C_4H_9$. This produces 0.58 g of a solid which melts at 78° C. and whose NMR and VPC analyses show that it corresponds to the isomers of formulae:

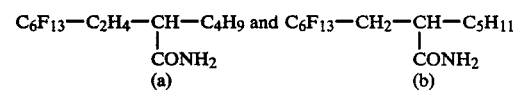

in the ratio a/b equal to 1.39.

EXAMPLE 3

Preparation of 1,1,1,2,2,3,3,4,4,5,5,6,6,7,7,8,8-heptadecafluoropentadecane 10- and 11-carboxamides Proceeding as in Example 1, starting with 1.032 g of the fluoroolefin $C_8F_{17}$—$CH_2$—CH=CH—$C_4H_9$, produces 0.98 g of a solid which melts at 88° C. and whose NMR and VPC analyses show that it corresponds to the isomers of formulae:

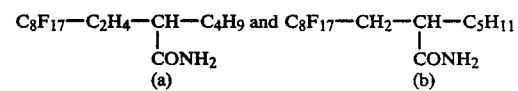

in the ratio a/b equal to 1.22.

EXAMPLE 4

Preparation of 1,1,1,2,2,3,3,4,4,5,5,6,6,7,7,8,8-heptadecafluoroeicosane 9- and 10-carboxamides Proceeding as in Example 1 and starting with 1.2 g of the fluoroolefin $C_8F_{17}$—CH=CH—$C_{10}H_{21}$, produces 0.82 g of a solid which melts at 92° C. and which corresponds to the isomers of formulae:

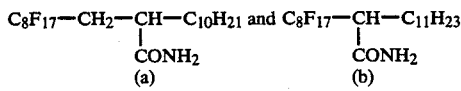

in the ratio a/b equal to 7.71.

EXAMPLE 5

Preparation of 1,1,1,2,2,3,3,4,4-nonafluoropentadecane 6- and 7-carboxamides

A microemulsion prepared from:
0.26 g of the fluoroolefin $C_4F_9-CH_2-CH=CH-C_8H_{17}$
1.48 g of formamide
1.63 g of 2-perfluorobutylethanol
1.63 g of polyethoxylated nonylphenol (10.5 moles of ethylene oxide per mole of nonylphenol) and
0.18 ml of acetone
is introduced into a pyrex tube.

After degassing with argon and irradiation for two days as in Example 1, the VPC injection of the microemulsion shows the presence of the following isomers:

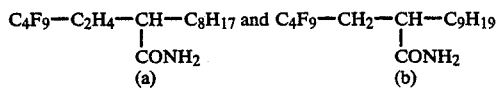

in a ratio a/b equal to 0.95.

EXAMPLE 6

Preparation of 1,1,1,2,2,3,3,4,4,5,5,6,6,7,7,8,8-heptadecafluoroeicosane 9- and 10-carboxamides In order to prepare the amides:

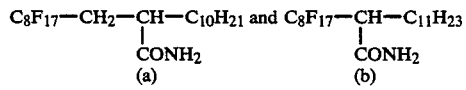

the procedure is as in Example 5, with 0.26 g of the fluoroolefin $C_8F_{17}-CH=CH-C_{10}H_{21}$, using 1.63 g of four polyethoxylated nonylphenols differing form each other in the number of ethylene oxide repeat units (EON).

The results obtained are collated in the following table:

| EON | Ratio a/b | Yield (%) |
| --- | --- | --- |
| 6 | 0.42 | 71.3 |
| 8 | 0.74 | 31.5 |
| 10 | 0.40 | 80.4 |
| 12 | 0.44 | 88.4 |

In another series of tests with the same fluoroolefin $C_8F_{17}-CH=CH-C_{10}H_{21}$, the polyethoxylated nonylphenol was replaced with the same quantity (1.63 g) of the nonionic fluorinated surfactant $C_6F_{13}C_2H_4(OC_2H_4)_{12}-OH$, on the one hand, and 2-perfluorobutylethanol was replaced by the same quantity (1.63 g) of various hydrogenated alcohols (1-hexanol, 1-heptanol and 1-octanol), on the other hand. The results obtained appear in the following table:

| Hydrogenated alcohol | Ratio a/b | Yield (%) |
| --- | --- | --- |
| 1-Hexanol | 0.25 | 87.8 |
| 1-Heptanol | 0.26 | 87.7 |
| 1-Octanol | 0.29 | 84.2 |

EXAMPLE 7

Preparation of 1,1,1,2,2,3,3,4,4,5,5,6,6,7,7,8,8-heptadecafluoroeicosane-N-methyl 9- and 10-carboxamides Proceeding as in Example 1 and starting with 1.2 g of the fluoroolefin $C_8F_{17}-CH=CH-C_{10}H_{21}$ and 8.65 ml of N-methylformamide produces 1.1 g of a paste which melts at a temperature below 50° C. and which corresponds to the isomers:

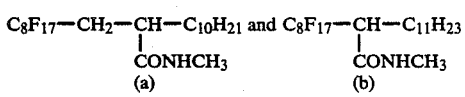

in a ratio a/b equal to 1.08.

EXAMPLE 8

Preparation of 1,1,1,2,2,3,3,4,4,5,5,6,6,7,7,8,8-heptadecafluoroeicosane-N-methyl 9- and 10-carboxamides A microemulsion prepared from:
0.26 g of the fluoroolefin $C_8F_{17}-CH=CH-C_{10}H_{21}$
1.48 g of N-methylformamide
1.63 g of 2-perfluorobutylethanol
1.63 g of polyethoxylated nonylphenol (12 moles of ethylene oxide per mole of nonylphenol) and
0.18 ml of acetone
is introduced into a pyrex tube.

After degassing with argon and irradiation for two days as in Example 1, injection of the microemulsion shows the presence of the following isomers:

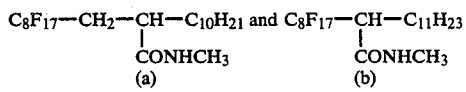

in a ratio a/b equal to 0.55.

EXAMPLE 9

Preparation of 1,1,1,2,2,3,3,4,4,5,5,6,6,7,7,8,8-heptadecafluoroeicosane-N,N-dimethyl 9- and 10carboxamides Proceeding as in Example 1 and starting with 1.2 g of the fluoroolefin $C_8F_{17}-CH=CH-C_{10}H_{21}$ and 11.4 ml of N,N-dimethylformamide produces 1.11 g of an oil which corresponds to the isomers of formulae:

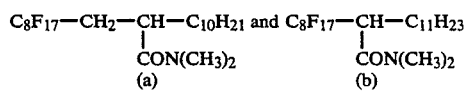

in a ratio a/b equal to 1.01.

The olefin $C_8F_{17}-CH=CH-C_{10}H_{21}$ employed in Examples 4 and 6-9 was prepared as follows: 546 g of perfluorooctyl iodide and 5 g of azobisisobutyronitrile are placed in a 1-liter reactor equipped with a stirrer, a reflux condenser and a dropping funnel. The mixture is heated to 75° C. and 261 g of 1-dodecene are then introduced over one hour. After 6 hours' reaction, 2.5 g of azobisisobutyronitrile are added and heating is then continued for 4 hours at 75° C. The reaction mixture is then distilled to remove the excess perfluorooctyl iodide and dodecene (110°–160° C. at 2,666 Pa), and then a solution of 68 g of potassium hydroxide in 250 ml of ethanol is added over 4 hours to the 678 g of remaining product, while the temperature is maintained at 40°–45° C. After addition of 1 liter of water and settling, the organic phase (563 g) is separated off and the olefin produced in this manner is purified by vacuum distillation (120° C./133 Pa).

EXAMPLE 10

Preparation of 1,1,1,2,2,3,3,4,4-nonafluoropentadecane 6- and 7-carboxylic acids A mixture of 125 mg of the solid obtained in Example 1, 2 ml of water and 2 g of sodium hydroxide pellets is heated for 24 hours at 130° C. in a round flask supporting a reflux condenser. After cooling, the pH of the reaction mixture is brought down to 1 by the addition of 4.2 ml of 37% strength hydrochloric acid and the mixture is left for 3 hours with stirring.

After extraction of the aqueous phase with 1,1,2-trichloro-1,2,2-trifluoroethane followed by evaporation of the solvent, 52 mg of a yellow oil are obtained, its analyses showing that it consists of the acids of formulae:

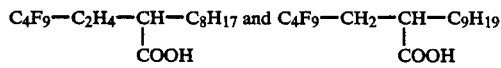

IR spectrum: 2960 (free OH); 1711 (C=O); 1460 (C—H α $CO_2H$); 1236 (C—F).

$^1$H NMR spectrum ($CD_3COCD_3$): 0.77 (3 p, m, $CH_3$); 1.16 (14 p, m, $CH_2$); 2.14 (1 p, m, CH); 3.25 (4 p, m, $CH_2$ α and β $CF_2$).

$^{19}$F NMR spectrum ($CD_3COCD_3$): −5.59 (3 f, m, $CF_3$); −38.83 (2 f, m, $CF_2$ α $CH_2$); −48.61 (2 f, m, $CF_2$ α $CH_2$); −50.36 (2 f, m, $CF_2$ α $CF_3$).

EXAMPLE 11

Preparation of 1,1,1,2,2,3,3,4,4,5,5,6,6-tridecafluorotridecane 8- and 9-carboxylic acids The procedure is as in Example 10, but with 138 mg of the solid obtained in Example 2. 100 mg of a yellow oil are recovered, consisting of the acids:

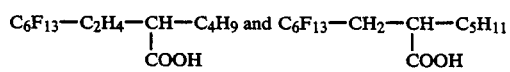

IR spectrum: 2969 (free OH); 1714 (C=O); 1460 (CH α $CO_2H$); 1208 (C—F).

EXAMPLE 12

Preparation of 1,1,1,2,2,3,3,4,4,5,5,6,6,7,7,8,8-heptadecafluoroeicosane 9- and 10-carboxylic acids Proceeding as in Example 10 with 189 mg of the solid from Example 4 produces 63 mg of a yellow oil consisting of the acids:

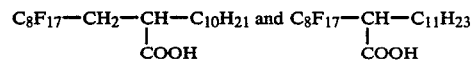

IR spectrum: 2960 (free OH); 1720 (C=O); 1470 (CH α $CO_2H$); 1200 (C—F).

$^1$H NMR spectrum ($CD_3COCD_3$): 0.92 (3 p, m, $CH_3$); 1.30 (18 p, m, $CH_2$); 2 (1 p, m, CH); 2.87 (2 p, m, $CH_2$ α $CF_2$).

$^{19}$F NMR spectrum ($CD_3COCD_3$): −5.27 (3 f, m, $CF_3$); −37.34 (2 f, m, $CF_2$ α $CH_2$); −46.06 (6 f, m, $CF_2$); −46.69 (2 f, m, $CF_2$ γ $CF_3$); −47.75 (2 f, m, $CF_2$ β $CF_3$); −50.35 (2 f, m, $CF_2$ α $CF_3$).

We claim:

1. Polyfluoro compounds comprising:

in which $R_F$ denotes a linear or branched perfluoroalkyl radical containing from 1 to 20 carbon atoms, $R_H$ denotes a linear or branched alkyl radical containing from 4 to 18 carbon atoms, m is integer from 0 to 2 and X denotes an OH or $NR_1R_2$ group in which $R_1$ and $R_2$, which are identical or different, each denote a hydrogen atom or a methyl radical.

2. Compounds according to claim 1, in which X denotes a $NH_2$ group.

3. Compounds according to claim 1, in which the radicals $R_F$ and $R_H$ each contain from 4 to 12 carbon atoms.

4. Mixtures of two compounds according to claim 1 in which one of the compounds comprises the formula:

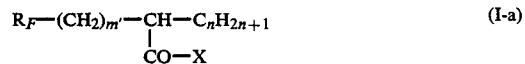

and the other comprises the formula:

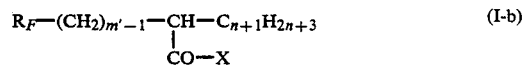

in which formula m' is equal to 1 or 2 and n is an integer from 4 to 17, and the molar ratio of I-a/I-b ranges from 0.1 to 10.

5. Method for preparing the polyfluoro compounds according to claim 1, comprising subjecting a polyfluoroolefin of general formula:

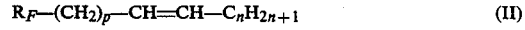

in which p is equal to 0 or 1 and n is an integer ranging from 4 to 17, to a photoamidation in the presence of an excess of formamide or of a methylated derivative thereof.

6. Method according to claim 5, in which the amide obtained is subjected to hydrolysis.

7. Method according to claim 5, in which a mixture containing the olefin (II) and formamide or its methylated derivative is subjected to an irradiation with ultraviolet rays in the presence of acetone as initiator.

8. Method according to claim 7, in which the operation is carried out in a homogeneous medium consisting of a solution of the olefin (II), of formamide and of acetone in an inert organic solvent.

9. Method according to claim 8, in which the solvent is tert-butanol.

10. Method according to claim 7, in which a microemulsion of the olefin (II), of formamide and of acetone, which is produced with the aid of a nonionic surface-active agent and of a cosurfactant agent of the alcohol type, one of these agents being fluorinated and the other unfluorinated, is subjected to the action of an UV radiation.

11. Method according to claim 10, in which the nonionic surface-active agent is chosen from ethoxylated alkyl-phenols, ethylene or propylene oxide polycondensates or ethoxylated polyfluoroalcohols.

12. Method according to claim 10, in which the cosurfactant agent is an aliphatic or fluoroaliphatic alcohol.

13. Method according to claim 10, in which the nonionic surface-active agent is a condensate of nonylphenol with 5 to 14 moles of ethylene oxide, and the cosurfactant agent is 2-perfluorobutylethanol.

14. Method according to claim 10, in which the nonionic surface-active agent is a condensate of 2-perfluorohexyl-ethanol with 10 to 15 moles of ethylene oxide, and the cosurfactant agent is 1-hexanol, 1-heptanol or 1-octanol.

15. Method according to claim 5, in which the molar ratio formamide/olefin (II) is between 10 and 120.

16. Method according to claim 15, in which the molar ratio formide/olefin (II) is between 40 and 90.

17. Method according to claim 7, in which the molar ratio acetone/formamide is between 0.03 and 0.2.

18. Method according to claim 17, in which the molar ratio acetone/formamide is between 0.05 and 0.09.

19. The mixture of claim 4, wherein the radical $R_F$ contains from 4 to 12 carbon atoms and n is an integer from 4 to 11.

* * * * *